United States Patent
Dorenkott et al.

Patent Number: 6,121,049
Date of Patent: Sep. 19, 2000

[54] METHOD OF VERIFYING ASPIRATED VOLUME IN AUTOMATIC DIAGNOSTIC SYSTEM

[75] Inventors: Jeffrey S. Dorenkott; Carl F. Panek, both of North Olmsted, Ohio

[73] Assignee: Bayer Corporation, Tarrytown, N.Y.

[21] Appl. No.: 09/329,918

[22] Filed: Jun. 10, 1999

Related U.S. Application Data

[63] Continuation-in-part of application No. 08/985,878, Dec. 5, 1997.

[51] Int. Cl.$^7$ ........................................ G01N 1/10
[52] U.S. Cl. ..................... 436/50; 436/54; 436/180; 422/67; 422/100; 422/108; 422/112; 73/1.74; 73/37; 73/864.01; 73/863.01
[58] Field of Search ................ 436/43, 54, 174, 436/50, 180; 422/63, 81, 100, 105, 108, 112; 73/1.74, 864.01, 863.01, 37

[56] References Cited

U.S. PATENT DOCUMENTS

| | | | |
|---|---|---|---|
| 4,780,833 | 10/1988 | Atake | 364/509 |
| 5,013,529 | 5/1991 | Itoh | 422/100 |
| 5,452,619 | 9/1995 | Kawanabe et al. | 73/864.01 |
| 5,463,895 | 11/1995 | Brentz | 73/61 R |
| 5,488,854 | 2/1996 | Kawanabe et al. | 73/19.05 |
| 5,488,874 | 2/1996 | Kawanabe et al. | 73/863.01 |
| 5,537,880 | 7/1996 | Takeda et al. | 73/864.25 |
| 5,540,081 | 7/1996 | Takeda et al. | 73/37 |
| 5,723,795 | 3/1998 | Merriam | 73/863 |

FOREIGN PATENT DOCUMENTS

| | | |
|---|---|---|
| 0215534 | 3/1987 | European Pat. Off. . |
| 0341438 | 11/1989 | European Pat. Off. . |
| 0658769 | 6/1995 | European Pat. Off. . |
| 0753750 | 1/1997 | European Pat. Off. . |
| 0810438 | 12/1997 | European Pat. Off. . |

OTHER PUBLICATIONS

Omar S. Khalil et al., "Abbott Prism: A Multichannel Heterogeneous Chemiluminescence Immunoassay Analyzer" *Clin. Chem.* 37/9, pp. 1540–1547 (1991).

*Primary Examiner*—Long V. Le
*Attorney, Agent, or Firm*—Weingarten, Schurgin, Gagnebin & Hayes LLP

[57] ABSTRACT

A method of verifying sample volume quantifies the fluid volume aspirated and verifies sample uniformity by detecting the presence of foam or clots in the sample. After aspiration, a pressure sensor is used to measure the vacuum needed to hold up the column of fluid in the probe tip. By knowing the geometry of the probe tip, the vacuum can be converted to a sample weight and volume, based on sample densities. Non-ideal conditions, such as foam on the surface of the fluid or a clot in the fluid, result in a sample volume much lighter, in the case of foam, or much greater, in the case of a clot, than anticipated. The method also determines the elapsed time of the aspiration. Foamy samples result in aspiration times shorter than normal. Clotted samples result in aspiration times longer than normal. Additionally, a determination can be made as to whether an error condition occurred. The error condition could be the occurrence of the sample fluid container becoming substantially empty of sample fluid during aspiration or the sample probe no longer being in contact with the fluid due to the probe not following a declining fluid level as the fluid is aspirated.

13 Claims, 3 Drawing Sheets

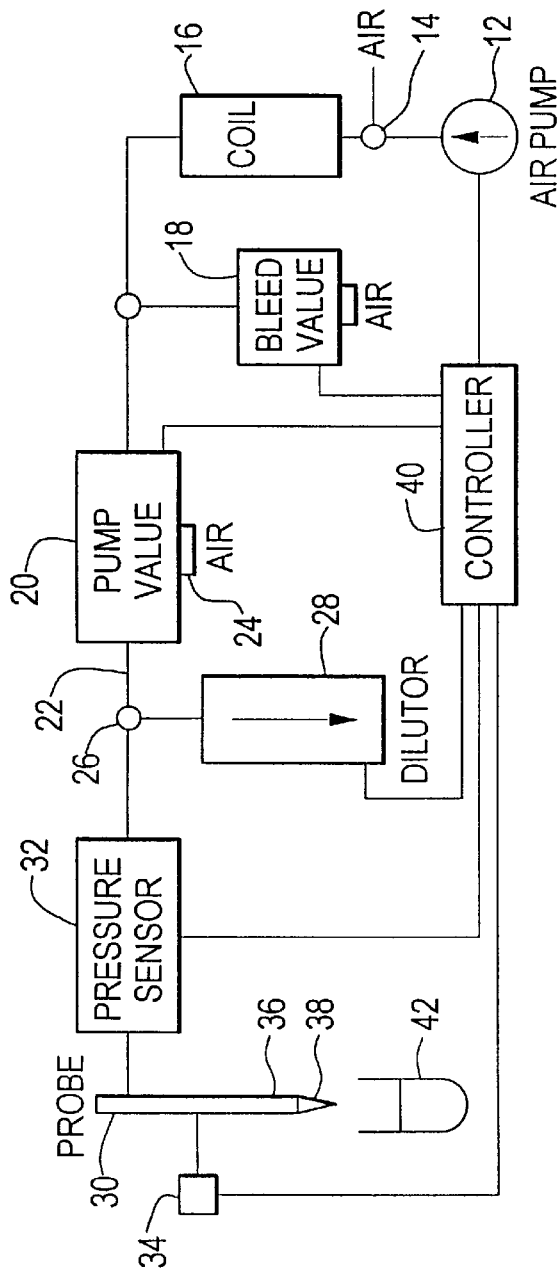
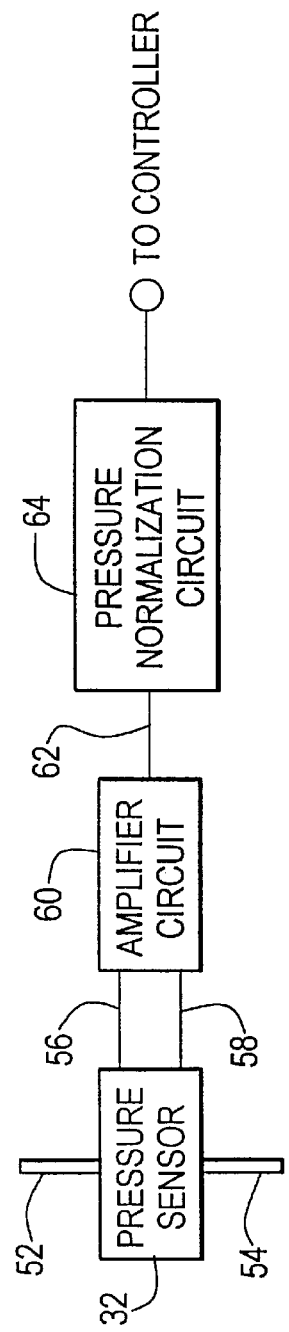
FIG. 1
FIG. 2

METHOD OF VERIFYING ASPIRATED VOLUME IN AUTOMATIC DIAGNOSTIC SYSTEM

RELATED APPLICATIONS

This application is a continuation-in-part of U.S. patent application Ser. No. 08/985,878 filed Dec. 5, 1997.

STATEMENT OF FEDERALLY SPONSORED RESEARCH

None

BACKGROUND OF THE INVENTION

Automated analyzers are used in clinical laboratories to measure various chemical constituents of body fluids, such as whole blood, blood serum, blood plasma, cerebral spinal fluid, urine, and the like obtained from patients. Automated analyzers reduce the number of trained technicians required to perform the analyses in a clinical laboratory, improve the accuracy of the testing, and reduce the cost per test.

Typically, an automated analyzer includes an automated fluid moving system which aspirates a sample of body fluid from a patient's specimen container and dispenses the sample into a reaction cuvette. The fluid moving system typically includes a pipette or sample probe on a robotically controlled arm to perform the aspiration and dispensing functions.

Chemical reagents, which are specific to the test being performed, are disposed into the sample-containing cuvette, thereby mixing the sample with the chemical reagents. By examining the reaction products resulting from the mixing of the sample and reagents, the automated analyzer determines the concentration of the specific chemical constituent being tested. Upon completion of the test, the automated analyzer typically prints the results of the test, including a sample identifier, a numerical result of the test, and a range of values for the chemical constituent as measured by the test.

During an aspiration operation, the robotic arm, under the command of a system controller, positions the sample probe above a specimen container and moves the probe into the container until the probe reaches the fluid in the container. A syringe type pump is activated to draw sample fluid from the specimen container into the probe. To ensure that accurate results are obtained in the tests, a consistent known volume of the sample must be accurately aspirated and delivered to the reaction cuvette. Under ideal conditions, motorized syringes can deliver the volume at the needed accuracy. However, conditions are not always ideal, so a method of verifying sample volume is needed.

Prior art methods have focused on detecting non-ideal conditions. In one method, pressure is measured after each increment of aspiration. A pressure value outside a predetermined pressure range signals heterogeneity in the sample. Khalil, Omar S. et al., "Abbott Prism: A Multichannel Heterogeneous Chemiluminescence Immunoassay Analyzer," *Clin. Chem.*, 37/9, 1540–47 (1991). European Patent Application No. 341,438 describes a system in which pressure is also monitored during aspiration. Bubbles, a clot, or a pressure leak are shown on a display screen as one or more spikes. European Patent Application No. 215,534 describes a system in which pressure after a suction operation is measured and compared to an expected normal value.

SUMMARY OF THE INVENTION

The present invention provides a method of verifying sample volume by quantifying the fluid volume aspirated and of verifying sample uniformity by detecting non-ideal conditions such as the presence of foam or clots in the sample.

A pressure sensor is used to measure the vacuum needed to hold up the column of aspirated fluid in the probe tip. This value is measured by determining the pressure difference between the start and the end of the aspiration. The pressures at the start and at the end of the aspiration are determined by looking for a significant rate of change in the pressure, upward at the start and downward at the end. By knowing the geometry of the probe tip, the pressure difference can be converted to a sample weight. The sample weight can be converted to a sample volume by assuming a sample density. The calculated volume can then be compared to the expected volume for a given probe geometry. Non-ideal conditions, such as foam on the surface of the fluid or a clot in the fluid, result in an apparent sample volume much lighter, in the case of foam, or much greater, in the case of a clot, than anticipated. Also, in the case of foam in the sample, the pressure decay begins much earlier than expected in a normal sample; in the case of a clot in the sample, the pressure decay begins much later than expected in a normal sample. Thus, a comparison of the measured elapsed time of the aspiration to the expected elapsed time provides another indication of sample non-uniformity.

The present method allows for a direct quantification of the amount of fluid aspirated. By making use of the rates of change of the pressure measurements, the present method is less susceptible to normal variances in fluid properties. Additionally, the present method makes use of a combined approach to verify that a correct amount of fluid is aspirated.

BRIEF DESCRIPTION OF THE DRAWINGS

The invention will be better understood by referring to the detailed description taken in conjunction with the following drawings, in which:

FIG. 1 is a schematic diagram of an aspirating and dispensing system according to the present invention;

FIG. 2 is a block diagram of a pressure sensor system;

DETAILED DESCRIPTION OF THE INVENTION

Figure 3:
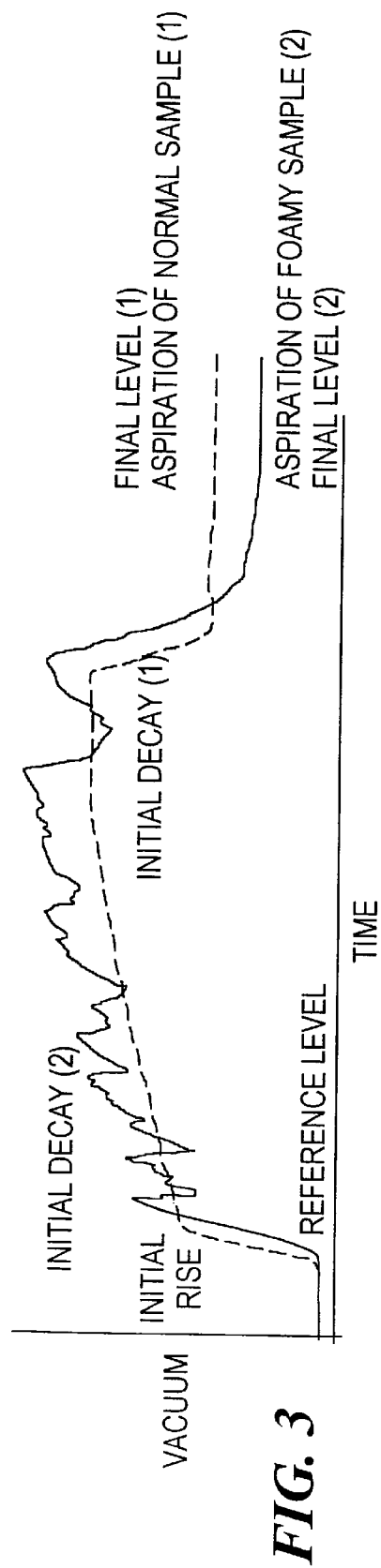
FIG. 3 is a graph of pressure (vacuum) versus time illustrating an aspiration of a normal sample (dashed line) and an aspiration of a foamy sample (solid line)

Referring to FIG. 1, aspirating and dispensing apparatus 10 includes an air source, such as an air pump 12 coupled through an air vent 14 to an accumulator 16. The air source should be able to provide a constant airflow at a predetermined rate and pressure. The air pump may be a small rotary type pump. The accumulator typically comprises a coil of long tubing wrapped around a cylinder and serves to dampen the pulsations from the pump. In this manner, the output from the accumulator is a consistent flow of air with few or no pulses.

A bleed valve 18 is located downstream of the accumulator. Downstream of the bleed valve is a pump valve 20. The pump valve is a three-way valve including a normally open port 22 to downstream and a normally closed port 24 to a vent. A tee connector 26 is coupled to the downstream port of the pump valve. One branch of the tee connector is coupled to a motorized syringe-type pump or dilutor 28 and the other branch of the tee connector is coupled to a sample probe 30.

A flow-through pressure sensor or transducer 32 is provided between the tee connector 26 and the sample probe 30. A suitable pressure sensor is manufactured by the Micro Switch Division of Honeywell Corporation identified as a 26PC Series pressure transducer. The sensitivity of the sensor corresponds to about 16 mV/psi of pressure difference. Other pressure sensors having suitable fluid and electrical characteristics can be used. Preferably, the pressure sensor is located close to the sample probe to improve the signal to noise ratio of the pressure measurements.

The sample probe is mounted on a robot arm 34. Typically, the probe includes a probe body 36 and a probe tip 38. The tip is usually disposable and removably coupled to the probe body. A supply of tips is stored where they are accessible by the probe upon movement by the robot arm. However, in some applications, a non-disposable tip permanently secured to the probe body may be used.

A system controller 40 is provided in communication with the air pump 12, bleed valve 18, pump valve 20, dilutor 28, and robot arm 34 to control operation of the system and with the pressure sensor 32 to receive pressure measurements. An aspirating and dispensing system of the present type is also described in application Ser. No. 08/501,806 filed on Jul.13, 1995, entitled METHOD AND APPARATUS FOR ASPIRATING AND DISPENSING SAMPLE FLUIDS, assigned to the assignee of this application. The disclosure of application No. 08/501,806 is incorporated by reference herein.

In operation during an aspiration, the air pump 12 is turned on, forcing air through the probe 30. The robot arm 34 positions the probe, with a probe tip attached, above a specimen container 42 and moves the probe into the container until the probe reaches the fluid therein. When the probe touches the fluid, the pressure sensor detects a rise in pressure. The air pump is turned off, and the bleed valve 18 is opened to depressurize the system. The pump valve 20 is then closed to isolate the pump 12 and the accumulator 16 from the probe 30 and the dilutor 28, and the dilutor is operated to draw a volume of the sample into the probe.

Referring to FIG. 2, the pressure sensor 32 includes a pair of fluid ports 52, 54 and a pair of electrical signal terminals 56, 58 coupled to an amplifier circuit 60. The air pressure measured at the sensor 32 provides a corresponding differential voltage signal to the amplifier circuit 60, which provides a single amplified output signal on a terminal 62. The amplifier circuit is preferably coupled to a pressure normalization circuit 64. The pressure normalization circuit, using sample and hold circuitry as is known in the art, normalizes the amplified pressure signal to a reference level, typically 0 volts, upon a signal from the controller. A relative pressure measurement is required when the system is to measure the amount of vacuum needed to hold up the column of fluid in the probe.

Figure 4:
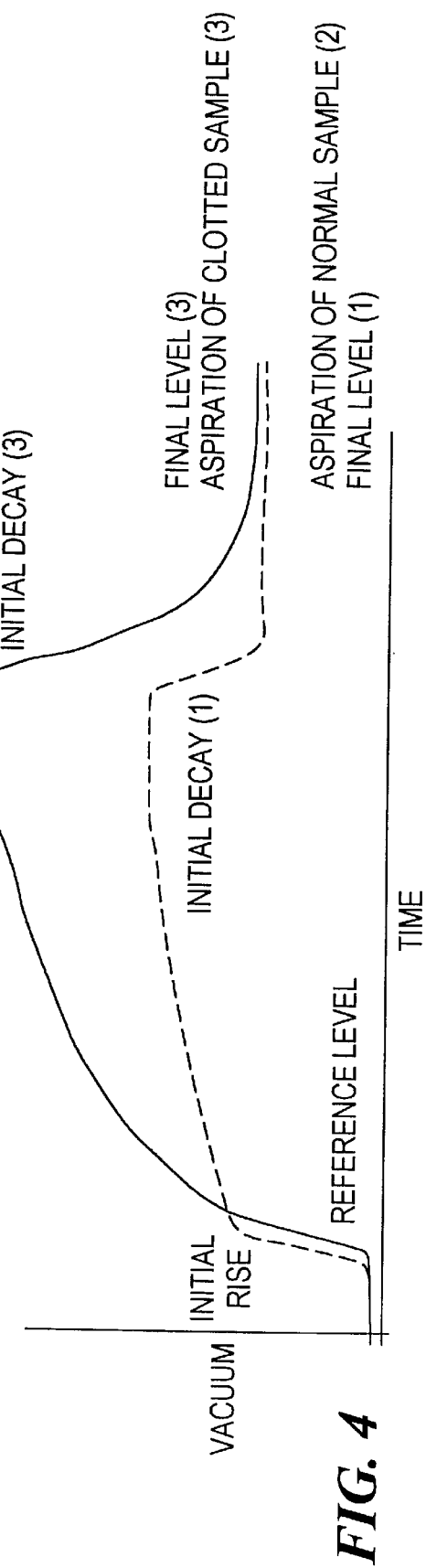
FIG. 4 is a graph of pressure (vacuum) versus time illustrating an aspiration of a normal sample (dashed line) and an aspiration of a clotted sample (solid line)

In determining the amount of vacuum needed to hold up the column of fluid, the pressure of the aspiration is measured over time. The pressure profile of a normal sample is illustrated in FIGS. 3 and 4, shown by a dashed line and the notation "Aspiration of Normal Sample (1)". Once the aspiration begins, an initial rise in vacuum from a reference level occurs. The pressure rise begins to level off, and after a period of time, the vacuum decays, indicated by the notation "Initial decay (1)" in FIGS. 3 and 4. The pressure comes to rest at a final level, indicated by the notation "Final Level (1)." This pressure is the amount of vacuum required to hold up the fluid in the probe.

From the measured pressure profile, four key reference values are determined:

1) $T_{rise}$, the time at which the initial rise in pressure signal occurs;

2) $P_{init}$, the vacuum pressure just prior to the initial vacuum rise, preferably normalized to 0 psi;

3) $T_{decay}$, the time at which the initial decay in pressure signal occurs; and 4) $P_{final}$, the vacuum pressure at a specified time after the initial decay.

The two time-based reference values, $T_{rise}$ and $T_{decay}$, are preferably determined numerically by examining the pressure sensor for the first significant upward and downward pressure changes respectively. The pressure sensor is sampled at predetermined time intervals, such as, for example, every 2 msec. The pressure changes are triggered, for example, by a rate of change of about 1 psi/sec occurring over a 3–4 msec time period. The starting time of each change is recorded, and the elapsed time for the aspiration is calculated as the difference between these two times.

For example, in a normal aspiration of about 100 μl, $P_{final}$ may be about 0.07 psig (where $P_{init}$ has been normalized to 0 psi). The elapsed time may be about 500 msec. The average pressure change over the aspiration is about 0.14 psi/sec. Trise and $T_{decay}$ are therefore triggered by pressure changes of about 10 times the expected average pressure change over the aspiration.

The pressure reading $P_{init}$ is taken just prior to the starting time of the initial rise. The pressure reading $P_{final}$ is taken at a specified time after the initial decay. Typically, this reading is taken 300 msec after the initial decay to allow for stabilization of the system. To better characterize the pressure readings, it is preferable to determine a time-averaged value for each reading. The time-averaged readings are determined numerically by averaging the pressure readings over a predetermined time interval, such as 50 to 100 msec.

The difference between the pressure reading $P_{init}$ and the pressure reading $P_{final}$ is recorded as the pressure change for the aspiration. The pressure change for the aspiration is used to determine the volume of fluid in the sample tip. This can be done if both the density of the fluid and the geometry of the sample tip are known. The pressure difference, $P_{final}-P_{init}$, can be converted into a fluid column height if the density is known. The fluid volume can be calculated from the fluid column height based on the geometry of the sample tip. Densities for various samples, such as blood serum, are generally known. For samples which may typically have a known range of densities, a mid point within the known range may be chosen for the calculation. Non-ideal conditions, such as foam on the sample surface or clots in the sample result in calculated volumes out of the anticipated values. Foam results in a sample volume less than expected. A clot results in a sample volume greater than expected.

FIG. 3 also illustrates a pressure profile of a foamy sample, shown by the solid line and the notation "Aspiration of Foamy Sample (2)," which results in a low calculated aspiration volume. In this case, the initial decay, indicated by "Initial Decay (2)," occurs shortly after the initial rise. The elapsed time of the aspiration is thus less than normal. Also, the final pressure reading, indicated by "Final Level (2)," is less than the final pressure reading of a normal sample.

FIG. 4 also illustrates a pressure profile of a clotted sample, shown by the solid line and the notation "Aspiration of Clotted Sample (3)," which results in a high calculated aspiration volume. In this case, the pressure reading continues to rise to a value greater than expected from a normal sample before decaying, indicated by "Initial Decay (3)." The final pressure reading, indicated by "Final Level (3)," is greater than the final pressure reading of a normal sample.

Upon detection of a volume or an elapsed time different than that expected for a particular sample, the system provides a signal, which may be a visible or audible alarm. The calculation of sample volume and elapsed time may be implemented in any suitable manner, such as by a programmed microprocessor or by circuitry.

Figure 5:
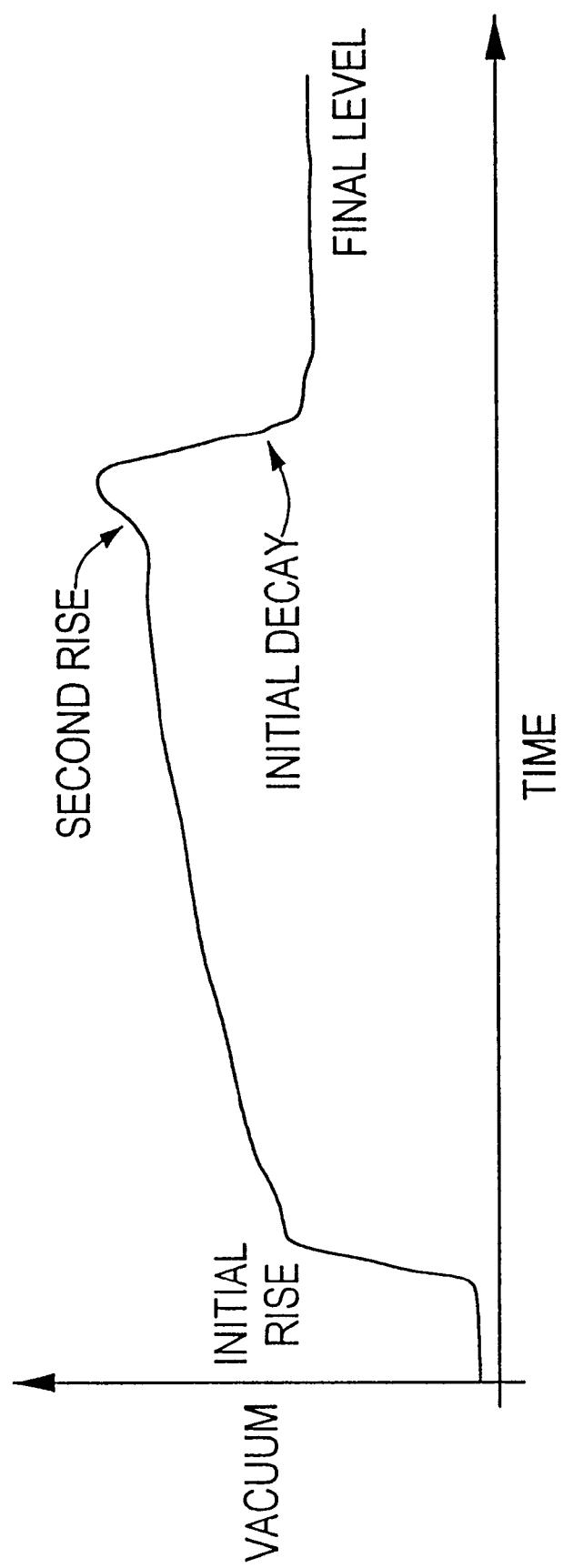
FIG. 5 is a graph of pressure (vacuum) versus time illustrating an aspiration during which the sample container become empty.

Referring now to FIG. 5, a pressure profile is illustrated wherein an error condition has been encountered. As shown in the pressure profile, a second rise in pressure is indicated after the initial rise and before the initial decay. The second rise in pressure is indicative that an error condition has occurred. The error condition may be that substantially all of the sample fluid has been aspirated from the sample container before the aspiration cycle has completed, that the probe has ceased being in contact with the fluid due to the probe not following the declining fluid level as the fluid is aspirated. or other conditions. This occurrence of an error condition is detected by performing a mathematical analysis of the pressure profile, such as by taking a second derivative on the pressure profile and obtaining a non-zero result. In contrast, a second order analysis of a normal aspiration curve, such as shown in FIGS. 3 and 4, will result in a substantially zero result. Upon detection of an error condition the system provides an indication of this condition, which may be a visible or audible alarm.

Having shown the preferred embodiment, those skilled in the art will realize many variations are possible which will still be within the scope and spirit of the claimed invention. Therefore, it is the intention to limit the invention only as indicated by the scope of the claims.

We claim:

1. A method for verifying an aspirated volume of fluid, comprising:

placing a sample probe within a container of a sample fluid, the sample probe having a predetermined geometry and the sample fluid having a predetermined assumed density;

drawing a vacuum within the sample probe to cause fluid to be drawn into the sample probe to aspirate the fluid;

measuring the pressure within the sample probe during aspiration of the fluid to obtain a pressure profile; and determining the presence of a second rise in vacuum of the pressure profile by taking a second derivative of the pressure profile to detect a rate of change of vacuum of at least a predetermined value for a predetermined period of time, wherein said second rise in vacuum is indicative of an error condition.

2. The method of claim 1 wherein said error condition comprises said container of sample fluid being substantially empty of said sample fluid during aspiration.

3. The method of claim 1 wherein said error condition comprises the sample probe no longer being in contact with the fluid due to the probe not following a declining fluid level as the fluid is aspirated.

4. The method of claim 1, further comprising the step of providing an indication when the presence of a second rise in vacuum of the pressure profile is determined.

5. The method of claim 1 wherein the step of taking a second derivative of the pressure profile provides a non-zero result.

6. The method of claim 4 wherein the step of providing an indication further comprises providing a audible indication.

7. The method of claim 4 wherein the step of providing an indication further comprises providing a visual indication.

8. A method for verifying an aspirated volume of fluid, comprising:

placing a sample probe within a container of a sample fluid, the sample probe having a predetermined geometry and the sample fluid having a predetermined assumed density;

drawing a vacuum within the sample probe to cause fluid to be drawn into the sample probe to aspirate the fluid;

measuring the pressure within the sample probe during aspiration of the fluid to obtain a pressure profile;

determining the presence of a second rise in vacuum of the pressure profile by taking a second derivative of the pressure profile and obtaining a non-zero result, wherein said non-zero result is indicative of an error condition; and providing an indication when the non-zero result is obtained.

9. The method of claim 8 wherein said error condition comprises said container of sample fluid being substantially empty of said sample fluid during aspiration.

10. The method of claim 8 wherein said error condition comprises the sample probe no longer being in contact with the fluid due to the probe not following a declining fluid level as the fluid is aspirated.

11. A method for verifying an aspirated volume of fluid, comprising:

placing a sample probe within a container of a sample fluid, the sample probe having a predetermined geometry and the sample fluid having a predetermined assumed density;

drawing a vacuum within the sample probe to cause fluid to be drawn into the sample probe to aspirate the fluid;

measuring the pressure within the sample probe during aspiration of the fluid to obtain a pressure profile;

determining a time of an initial rise in vacuum of the pressure profile by detecting a rate of change of vacuum of at least a predetermined value for a predetermined period of time;

determining the presence of a second rise in vacuum of the pressure profile by detecting a rate of change of vacuum of at least a predetermined value for a predetermined period of time by taking a second derivative of the pressure profile and obtaining a non-zero result, and wherein said non-zero result is indicative of an error condition; and providing an indication when the presence of a second rise in vacuum of the pressure profile is determined.

12. The method of claim 11 wherein said error condition comprises said container of sample fluid being substantially empty of said sample fluid during aspiration.

13. The method of claim 11 wherein said error condition comprises the sample probe no longer being in contact with the fluid due to the probe not following a declining fluid level as the fluid is aspirated.

* * * * *